US010124161B2

(12) United States Patent
Barker

(10) Patent No.: US 10,124,161 B2
(45) Date of Patent: Nov. 13, 2018

(54) NEUROSTIMULATION LEAD WITH CONDUCTIVE ELEMENTS AND METHODS FOR MAKING THE SAME

(71) Applicant: Boston Scientific Neuromodulation Corporation, Valencia, CA (US)

(72) Inventor: John M. Barker, Thousand Oaks, CA (US)

(73) Assignee: BOSTON SCIENTIFIC NEUROMODULATION CORPORATION, Valencia, CA (US)

( * ) Notice: Subject to any disclaimer, the term of this patent is extended or adjusted under 35 U.S.C. 154(b) by 0 days.

(21) Appl. No.: 15/476,328

(22) Filed: Mar. 31, 2017

(65) Prior Publication Data

US 2017/0281929 A1 Oct. 5, 2017

Related U.S. Application Data

(60) Provisional application No. 62/316,456, filed on Mar. 31, 2016.

(51) Int. Cl.

*A61N 1/00* (2006.01)
*A61N 1/05* (2006.01)

(Continued)

(52) U.S. Cl.

CPC ............ *A61N 1/0551* (2013.01); *A61N 1/05* (2013.01); *A61N 1/36146* (2013.01); *A61N 1/37235* (2013.01)

(58) Field of Classification Search

CPC ................................ A61N 1/0551; A61N 1/05

(Continued)

(56) References Cited

U.S. PATENT DOCUMENTS 3,239,916 A 3/1966 Lee
3,833,755 A 9/1974 Soelberg (Continued)

OTHER PUBLICATIONS

U.S. Appl. No. 12/410,320, Entitled: Multi-Conductor Ribbon for a Lead Assembly of an Implantable Electric Stimulation System and Methods of Making and Using, Inventor: Anne Margaret Pianca, filed Mar. 24, 2009, 33 pages.

(Continued)

*Primary Examiner* — Nadia A Mahmood
(74) *Attorney, Agent, or Firm* — Lowe Graham Jones PLLC; Bruce E. Black

(57) ABSTRACT

A lead includes a ribbon cable comprising a distal end portion and a proximal end portion. The ribbon cable has a plurality of conductors disposed within an insulating body and a plurality of electrode apertures selectively disposed along the distal end portion of the insulating body. The ribbon cable further includes a plurality of conductive electrodes, wherein each of the plurality of conductive electrodes is disposed over at least one of the plurality of electrode apertures and in electrical communication with at least one of the plurality of conductors. The lead may optionally include a flexible, flat lead body. A method of making a lead includes the steps of (1) obtaining a ribbon cable comprising a plurality of conductors; (2) selectively removing regions of the insulating body to create a plurality of apertures; and (3) placing a plurality of conductive elements over the plurality of apertures, respectively.

20 Claims, 9 Drawing Sheets

100 134 103 133 106 102 112 144 114 110 120

(51) Int. Cl.
*A61N 1/36* (2006.01)
*A61N 1/372* (2006.01)

(58) Field of Classification Search
USPC .......................................................... 607/116
See application file for complete search history.

(56) References Cited

U.S. PATENT DOCUMENTS

| | | | |
|---|---|---|---|
| 4,113,335 | A | 9/1978 | Lang et al. |
| 5,499,981 | A | 3/1996 | Kordis |
| 6,175,710 | B1 | 1/2001 | Kamaji et al. |
| 6,181,969 | B1 | 1/2001 | Gord |
| 6,224,450 | B1 | 5/2001 | Norton |
| 6,271,094 | B1 | 8/2001 | Boyd et al. |
| 6,295,944 | B1 | 10/2001 | Lovett |
| 6,364,278 | B1 | 4/2002 | Lin et al. |
| 6,391,985 | B1 | 5/2002 | Goode et al. |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |
| 7,203,548 | B2 | 4/2007 | Whitehurst et al. |
| 7,244,150 | B1 | 7/2007 | Brase et al. |
| 7,450,997 | B1 | 11/2008 | Pianca et al. |
| 7,596,414 | B2 | 9/2009 | Whitehurst et al. |
| 7,610,103 | B2 | 10/2009 | Whitehurst et al. |
| 7,672,734 | B2 | 3/2010 | Anderson et al. |
| 7,761,165 | B1 | 7/2010 | He et al. |
| 7,783,359 | B2 | 8/2010 | Meadows |
| 7,792,590 | B1 | 9/2010 | Pianca et al. |
| 7,809,446 | B2 | 10/2010 | Meadows |
| 7,949,395 | B2 | 5/2011 | Kuzma |
| 7,974,706 | B2 | 7/2011 | Moffitt et al. |
| 2003/0114905 | A1 | 6/2003 | Kuzma |
| 2004/0059392 | A1 | 3/2004 | Parramon et al. |
| 2005/0165465 | A1 | 7/2005 | Pianca et al. |
| 2006/0200218 | A1 | 9/2006 | Wahlstrand |
| 2007/0150007 | A1 | 6/2007 | Anderson et al. |
| 2007/0150036 | A1 | 6/2007 | Anderson |
| 2007/0161294 | A1 | 7/2007 | Brase et al. |
| 2007/0219595 | A1 | 9/2007 | He |
| 2007/0239243 | A1 | 10/2007 | Moffitt et al. |
| 2008/0071320 | A1 | 3/2008 | Brase |
| 2009/0187222 | A1 | 7/2009 | Barker |
| 2009/0276021 | A1 | 11/2009 | Meadows et al. |
| 2010/0076535 | A1 | 3/2010 | Pianca et al. |
| 2010/0268298 | A1 | 10/2010 | Moffitt et al. |
| 2011/0004267 | A1 | 1/2011 | Meadows |
| 2011/0078900 | A1 | 4/2011 | Pianca et al. |
| 2011/0130817 | A1 | 6/2011 | Chen |
| 2011/0130818 | A1 | 6/2011 | Chen |
| 2011/0238129 | A1 | 9/2011 | Moffitt et al. |
| 2011/0313500 | A1 | 12/2011 | Barker et al. |
| 2012/0016378 | A1 | 1/2012 | Pianca et al. |
| 2012/0046710 | A1 | 2/2012 | Digiore et al. |
| 2012/0071949 | A1* | 3/2012 | Pianca .................... A61N 1/05 607/59 |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | Digiore et al. |
| 2012/0203321 | A1 | 8/2012 | Moffitt et al. |
| 2012/0316615 | A1 | 12/2012 | Digiore et al. |
| 2013/0105071 | A1 | 5/2013 | Digiore et al. |

OTHER PUBLICATIONS

U.S. Appl. No. 62/316,456, Entitled: Neurostimulation Lead With Conductive Elements and Methods for Making the Same, Inventor: John M. Barker, filed Mar. 31, 2016, 33 pages.

U.S. Appl. No. 12/177,823, Entitled: Lead With Transition and Methods of Manufacture and Use, Inventor: Pianca et al., filed Jul. 22, 2008, 22 pages.

U.S. Appl. No. 13/750,725, Entitled: Systems and Methods for Identifying Circumferential Positioning of Electrodes of Leads for Electrical Stimulation Systems, Inventor: Pianca et al., filed Jan. 25, 2013, 36 pages.

U.S. Appl. No. 11/283,240, Entitled: Implantable Stimulator With Integrated Plastic Housing/Metal Contacts and Manufacture and Use, Inventor: He et al., filed Sep. 29, 2005, 19 pages.

* cited by examiner

NEUROSTIMULATION LEAD WITH CONDUCTIVE ELEMENTS AND METHODS FOR MAKING THE SAME

CROSS-REFERENCE TO RELATED APPLICATIONS

This application claims the benefit under 35 U.S.C. § 119(e) of U.S. Provisional Patent Application Ser. No. 62/316,456, filed Mar. 31, 2016, which is incorporated herein by reference.

FIELD

The present invention is directed to the area of implantable electrical stimulation systems and methods of making and implanting the same. More specifically, the present invention is directed to neurostimulation leads with conductive elements for an electrical stimulation system and methods of making the same.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a lead that includes a ribbon cable comprising a distal end portion and a proximal end portion. The ribbon cable has a plurality of conductors disposed within an insulating body and a plurality of electrode apertures selectively disposed along the distal end portion of the insulating body. The ribbon cable further includes a plurality of conductive electrodes, wherein each of the plurality of conductive electrodes is disposed over at least one of the plurality of electrode apertures and in electrical communication with at least one of the plurality of conductors.

In at least some embodiments, the lead further includes a plurality of conductive terminals selectively disposed along the proximal end portion of the insulating body, wherein each of the plurality of conductive terminals is in electrical communication with at least one of the plurality of conductors. In at least some embodiments, the lead may include a plurality of conductive terminals, wherein each of the plurality of conductive terminals is disposed over at least one of the plurality of terminal apertures and in electrical communication with at least one of the plurality of conductors. The ribbon cable may have a plurality of terminal apertures selectively disposed along the proximal end portion of the insulating body.

In at least some embodiments, the plurality of electrode apertures can be staggered with respect to each other in a longitudinal direction along the insulating body.

In at least some embodiments, at least one of the plurality of conductive electrodes is a conductive polymer electrode. The conductive polymer electrode can be made of a conductive epoxy. The conductive polymer electrode can be made of a polymeric material mixed with a conductive material.

In at least some embodiments, at least one of the plurality of conductive electrodes is a solid metallic electrode.

In at least some embodiments, the distal end portion of the ribbon cable is shaped in a generally planar configuration. The proximal end portion of the ribbon cable can be shaped in a cylindrical configuration. Optionally, at least one of the plurality of conductive electrodes can extend completely around the insulating body.

Another embodiment is an electrical stimulation system that includes a lead and a control module. The lead includes a ribbon cable and a plurality of electrodes. The ribbon cable has a distal end portion and a proximal end portion. The ribbon cable has a plurality of conductors disposed within an insulating body and a plurality of electrode apertures selectively disposed along the distal end portion of the insulating body. The ribbon cable further has a plurality of conductive electrodes, wherein each of the plurality of conductive electrodes is disposed over at least one of the plurality of electrode apertures and in electrical communication with at least one of the plurality of conductors. The control module includes a housing and an electronic subassembly disposed in the housing.

In at least some embodiments, at least one of the plurality of conductive electrodes is a conductive polymer electrode in the electrical stimulation system.

A further embodiment is a lead that includes a flexible, flat lead body comprising a distal end portion and a proximal end portion. The lead body has a plurality of conductors disposed within an insulation covering with the conductors lying parallel to each other along the distal end portion. The lead body further has a plurality of electrode apertures selectively disposed along the distal end portion of the insulation covering. The lead further includes a plurality of conductive electrodes, wherein each of the plurality of conductive electrodes is disposed over at least one of the plurality of electrode apertures and in electrical communication with at least one of the plurality of conductors.

In at least some embodiments, a plurality of conductive terminals are selectively disposed along the proximal end portion of the insulation covering, wherein each of the plurality of conductive terminals is in electrical communication with at least one of the plurality of conductors. Optionally, the lead body has a plurality of terminal apertures selectively disposed along the proximal end portion of the insulation covering. Optionally, each of the plurality of conductive terminals is disposed over at least one of the plurality of terminal apertures and in electrical communication with at least one of the plurality of conductors.

In at least some embodiments, a method of making a lead includes the steps of (1) obtaining a ribbon cable comprising a plurality of conductors disposed within an insulating body; (2) selectively removing regions of the insulating body to create a plurality of apertures that expose the plurality of conductors; and (3) placing a plurality of conductive elements over the plurality of apertures, wherein each conductive element is in electrical communication with each conductor in the ribbon cable, respectively. The method may optionally include applying a conductive polymeric material over the plurality of apertures.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and implanting the same. More specifically, the present invention is directed to neurostimulation leads with conductive polymer electrodes for an electrical stimulation system and methods of making the same.

Suitable implantable electrical stimulation systems include, but are not limited to, a least one lead with one or more electrodes disposed along a distal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent applications Ser. Nos. 12/177,823 and 13/750,725, all of which are incorporated by reference in their entireties.

Figure 1:
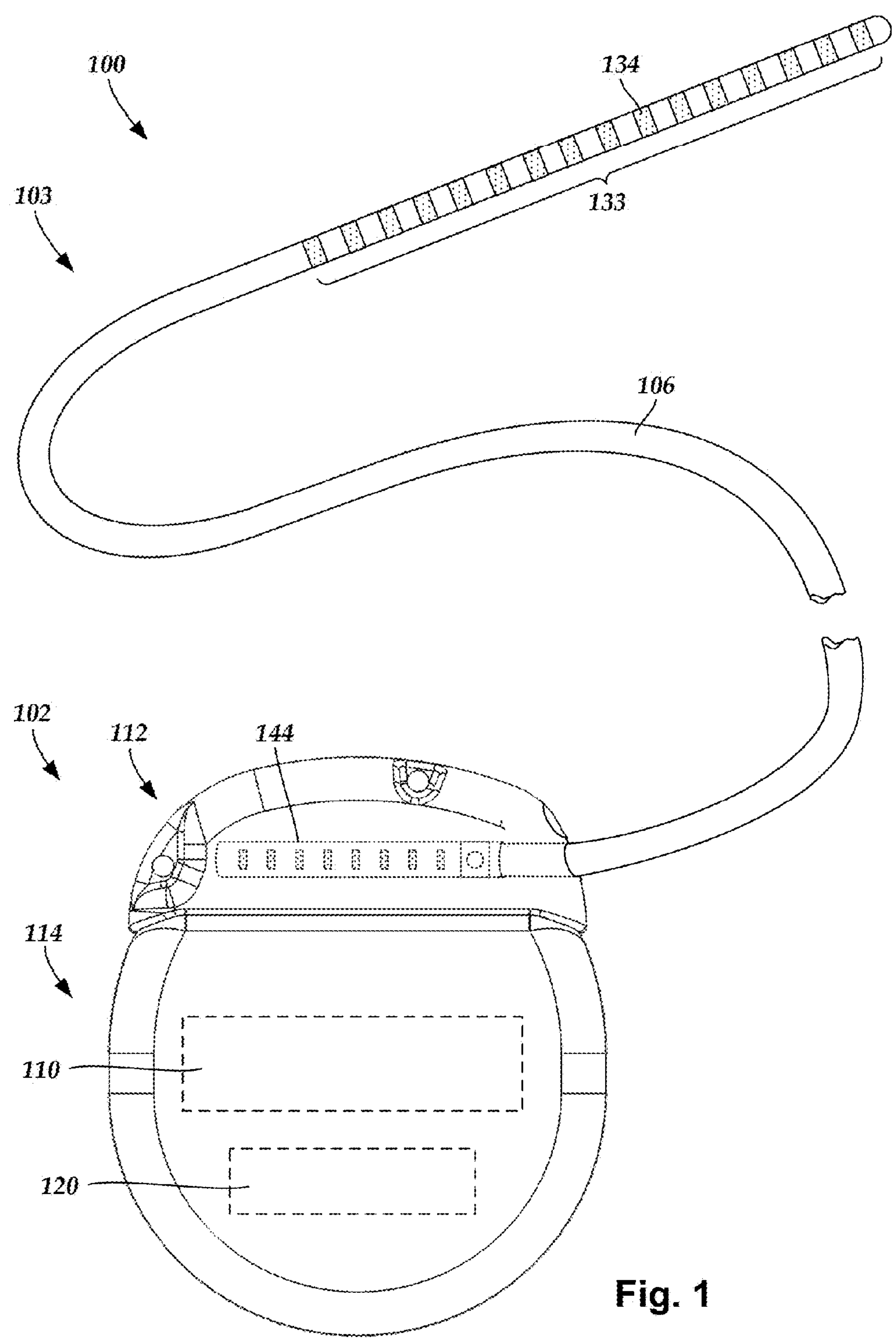
FIG. 1 is a schematic view of one embodiment of an electrical stimulation system that includes a lead electrically coupled to a control module according to an embodiment of the present invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. Stimulation circuitry 110 and an optional power source 120 are disposed in the electronics housing 114. A control module connector 144 is disposed in the connector housing 112. The control module connector 144 is configured and arranged to make an electrical connection between the lead 103 and the stimulation circuitry 110 of the control module 102.

The electrical stimulation system or components of the electrical stimulation system, including the lead body 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the lead body 106 are typically disposed in, or separated by, a non-conductive, biocompatible material such as, for example, silicone, polyurethane, polyetheretherketone ("PEEK"), epoxy, and the like or combinations thereof. The lead body 106 may be formed in the desired shape by any process including, for example, molding (including injection molding), casting, and the like. The non-conductive material typically extends from the distal end of the lead body 106 to the proximal end of the lead body 106.

Figure 2A:
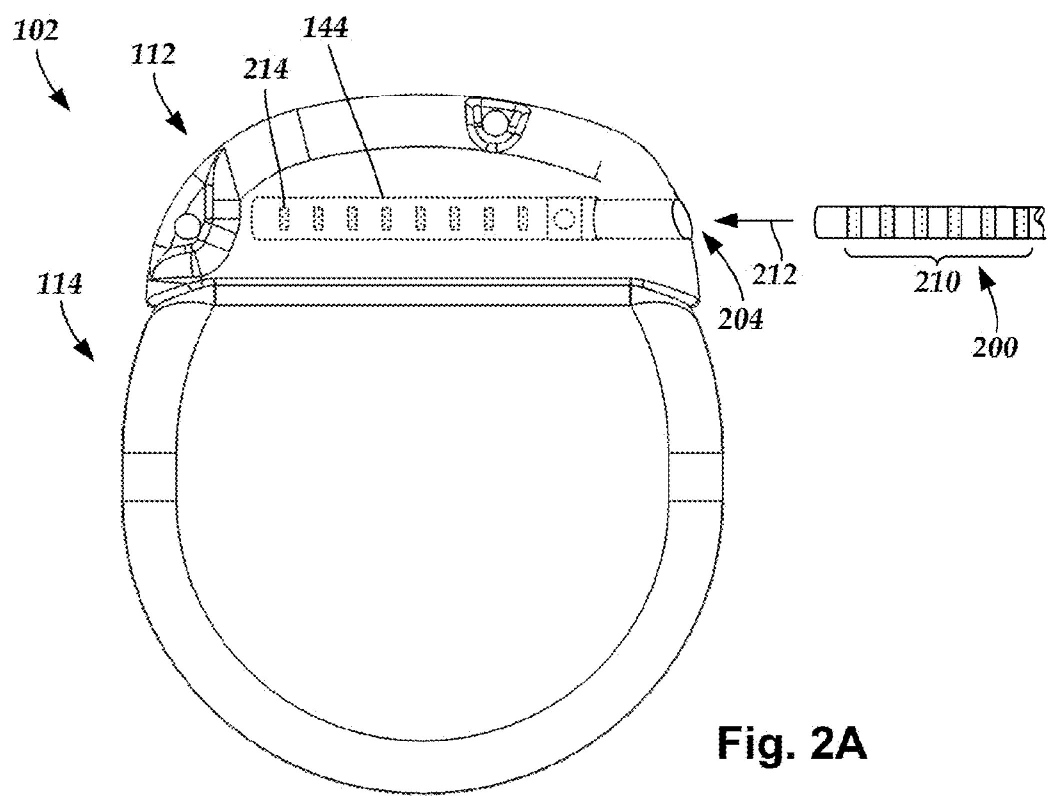
FIG. 2A is a schematic view of one embodiment of the control module of FIG. 1 configured and arranged to electrically couple to an elongated device according to an embodiment of the present invention.
Figure 2B:
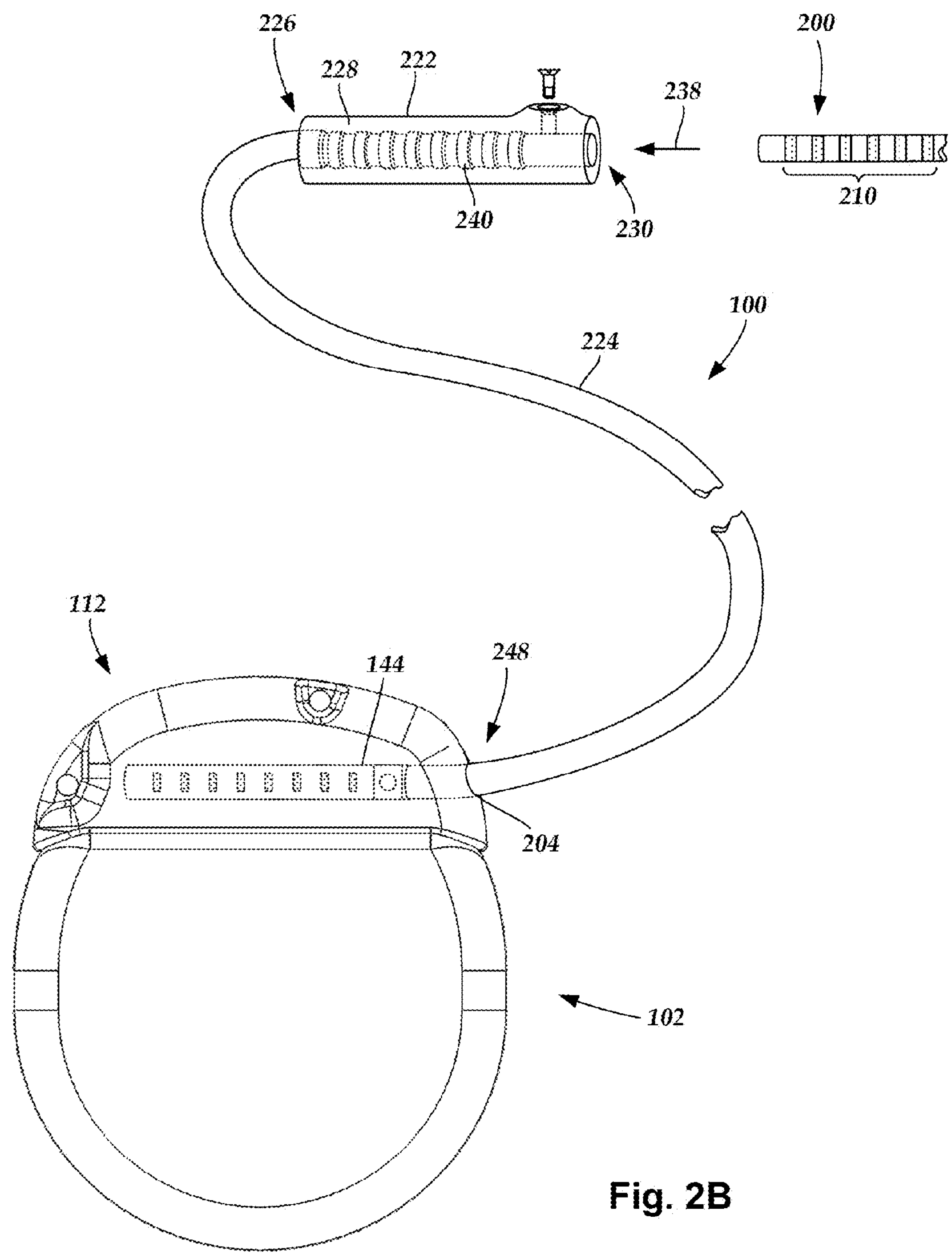
FIG. 2B is a schematic view of one embodiment of a lead extension configured and arranged to electrically couple the elongated device of FIG. 2A to the control module of FIG. 1 according to an embodiment of the present invention.

Terminals (e.g., 210 in FIGS. 2A-2B) are typically disposed along the proximal end of the lead body 106 of the electrical stimulation system 100 (as well as any splitters, lead extensions, adaptors, or the like) for electrical connection to corresponding connector contacts (e.g., 214 and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the lead body 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the lead extension 224 of FIG. 2B, an adaptor, or the like or combinations thereof), or a combination thereof.

The control module connector 144 defines at least one port into which a proximal end of the elongated device 200 can be inserted, as shown by directional arrow 212. In FIG. 2A (and in other figures), the connector housing 112 is shown having one port 204. The connector housing 112 can define any suitable number of ports including, for example, one, two, three, four, five, six, seven, eight, or more ports.

The control module connector 144 also includes a plurality of connector contacts, such as connector contact 214, disposed within each port 204. When the elongated device 200 is inserted into the port 204, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

In at least some instances, a large control module, such as the control module 102 illustrated in FIGS. 1-2B, is not desirable. A smaller, more compact control module may be suitable for situations such as, for example, short-term implantation (for example, 1 or 2 weeks, 1, 2, 3, 4, 6, 8, 12, or 18 months), short-term trial (for example, 1 or 2 weeks, 1, 2, 3, 4, 6, 8, 12, or 18 months), clinical studies (for example, for a period of 1 or 2 weeks, 1, 2, 3, 4, 6, 8, 12, or 18 months), or the like. Such a control module may also be useful when a less invasive surgical implantation is desired, recommended, or required. In some instances, a patient or clinician may be willing to charge the control module more frequently if the control module is smaller or the surgery is less invasive. In addition, there may be more options in the body of the patient for implantation of a smaller control module than are available for the larger control module (which is often implanted in the thoracic body cavity or the buttocks due to the size of the device.) A smaller control module may also be less expensive and particularly useful for trials to determine whether electrical stimulation is beneficial. In at least some embodiments, the electrical stimulation system with the smaller control module can be upgraded to an electrical stimulation system such as that illustrated in FIGS. 1-2B if the trial shows sufficient benefit to the patient. In at least some embodiments, the smaller control module may allow for the device to be MRI (magnetic resonance imaging) conditionally safe because of its implant location and size.

In some embodiments, the control module can be made smaller by permanently affixing the lead (or a lead extension) to the control module. For example, the lead can be hardwired to the stimulation circuitry so that the control module does not need a connector and header.

In at least some embodiments of the present invention, a neurostimulation lead includes a generally planar lead body with selectively disposed apertures that expose conductors within an insulation covering of the lead body. Conductive electrodes, terminals, or both are arranged to be into electrical communication with the exposed conductors. In at least some embodiments, at least one of the conductive electrodes, terminals, or both may take the form of a conductive polymer applied over at least one of the apertures. Some conventional neurostimulation leads may be include individual micro-conductors, multi-lumen tubing and machined electrodes made from materials such as platinum.

Figure 3A:
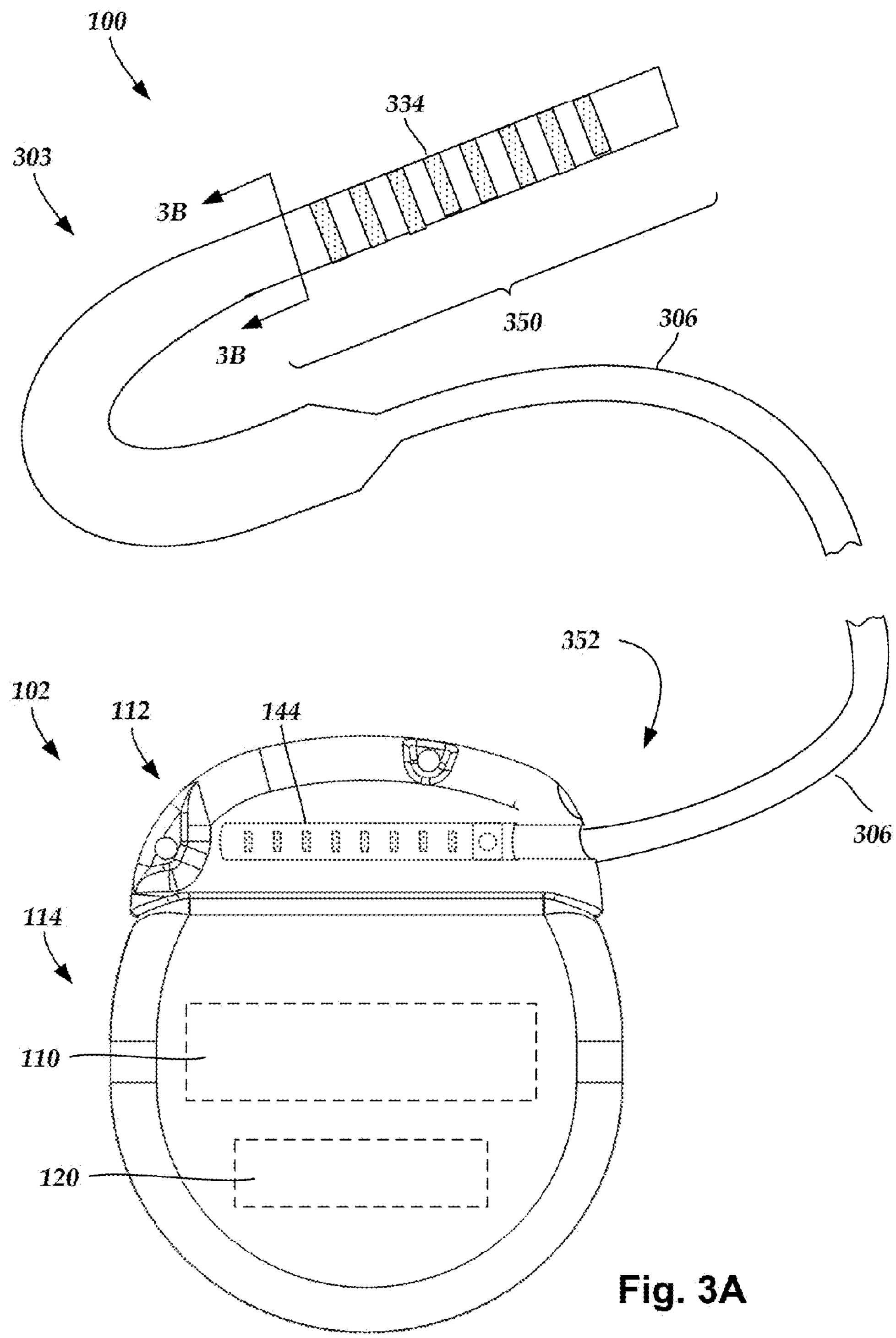
FIG. 3A is a schematic view of another embodiment of an electrical stimulation system using a ribbon cable according to an embodiment of the present invention.

FIG. 3A schematically illustrates the electrical stimulation system of FIG. 1 with a lead 303 including a ribbon cable 306 that extends between a distal end portion 350 and a proximal end portion 352. In at least some embodiments, the ribbon cable 306 may take the place of the lead body 106 (FIG. 1). In at least some embodiments, a plurality of conductive electrodes 334 are disposed along the distal end portion 350 and the electrodes 334 are in electrical communication with conductors within in the ribbon cable 306.

Figure 3B:
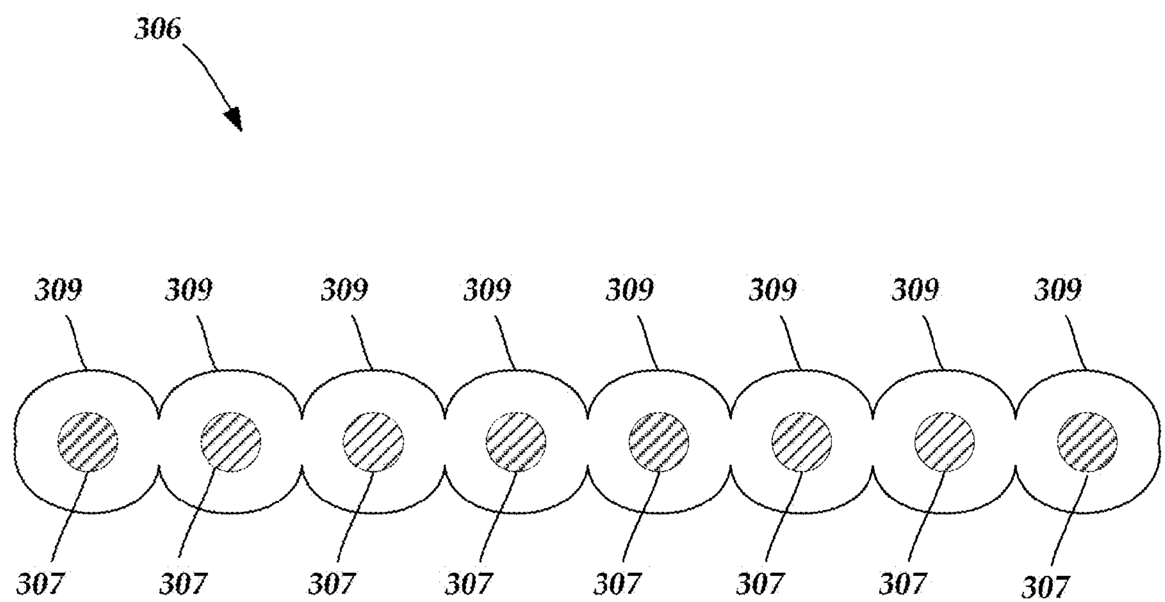
FIG. 3B is a cross-sectional view of the ribbon cable of FIG. 3A taken along line 3B-3B of FIG. 3A according to an embodiment of the present invention.

Turning to FIG. 3B, in at least some embodiments the ribbon cable 306 takes the form of a multi-conductor ribbon cable having multiple conductors 307 disposed in a non-conductive, biocompatible insulating body 309 made from materials such as, for example, silicone, polyurethane, polyetheretherketone ("PEEK"), epoxy, and the like or combinations thereof. The ribbon cable 306 may be generally flat or planar or may have another shape such as, but not limited to, circular or elliptical. In at least some embodiments, the ribbon cable 306 (or a portion of the ribbon cable) can be twisted or otherwise configured with a multi-revolution spiral or helical configuration capable of interacting with (for example, winding around) a target anatomy such as, but not limited to, a dorsal root ganglion, a dorsal nerve root, a ventral nerve root or some other anatomical feature targeted for neurostimulation.

In at least some embodiments, the ribbon cable 306 has conductors 307 that are lying parallel to each other in one or more layers. The ribbon cable 306 may include multiple layers of insulating bodies 309 and conductors 307. The ribbon cable 306 or portions thereof can be color coded or end coded to make it easier to identify individual conductors. Ribbon cables can be specified by the spacing or pitch of the conductors 307 and the number of conductors. In at least some embodiments, the ribbon cable 306 may be purchased in bulk and cut to a desired length. Additionally or alternatively, the ribbon cable 306 may take a variety of configurations with respect to the pitch, number of conductors, insulating body material, conductor material, or any combination thereof. The conductors in the ribbon cable can be a single filer metal wire or can be a multi-filer cable for increased fatigue performance.

Figure 4:
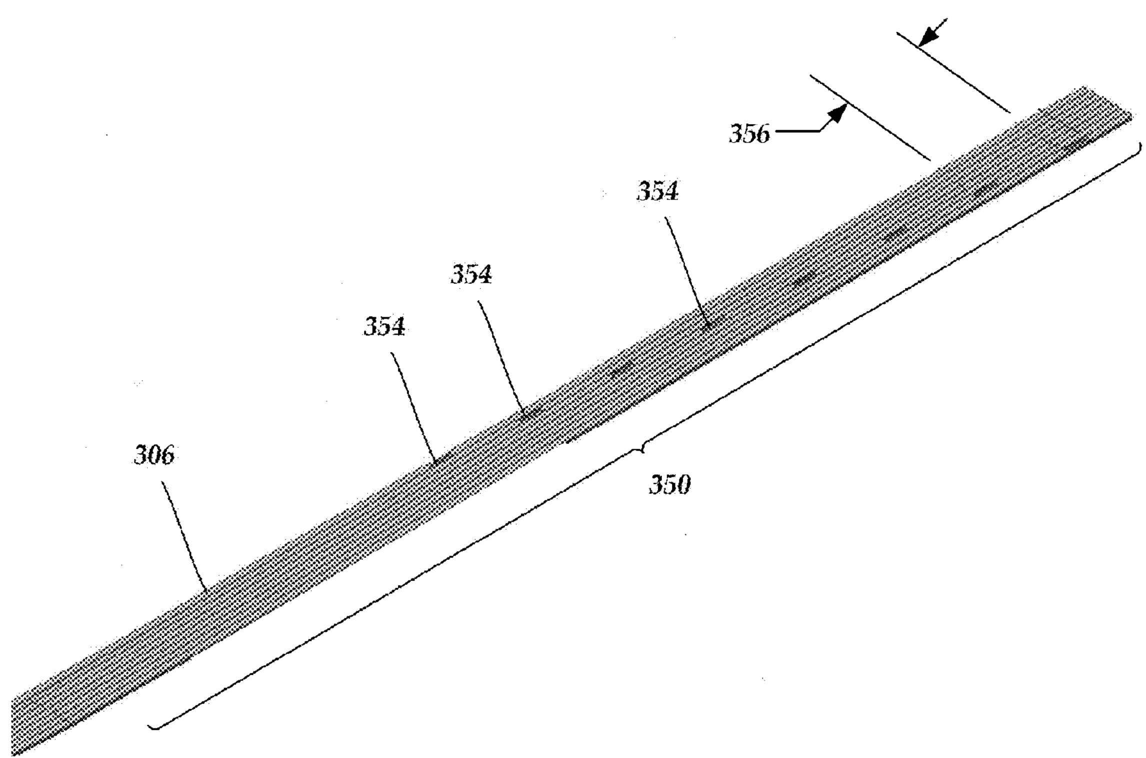
FIG. 4 is a schematic, perspective view of a ribbon cable having a plurality of windows according to an embodiment of the present invention.

FIG. 4 schematically illustrates the distal end portion 350 of the ribbon cable 306. At various places along the distal end portion 350, regions, windows or apertures 354 of insulation material are selectively removed to expose the metal conductors underneath. The apertures 354 may be spaced or staggered according to a desired pitch 356 (e.g., a desired distance from one aperture to an adjacent aperture in a lateral direction, a longitudinal direction, or both). In the illustrated embodiment, a single aperture 354 exposes a single metal conductor. In at least some embodiments, multiple apertures may be created to expose a common conductor, which in turn would permit a plurality of electrodes to be in electrical communication with the common conductor. The apertures may be on one or both sides of the ribbon cable.

In at least some embodiments, the apertures 354 can be created using a mechanical skiving technique, a laser ablation technique, or some other technique capable of selectively removing regions of the insulation material to expose the conductors, and thus create the apertures 354. Additionally or alternatively, the proximal end portion 352 may be processed in a similar manner to expose the conductors in the ribbon cable 306 for coupling to the plurality of terminals 210 (FIG. 2A). The proximal contact array could terminate in an electrical connector (e.g., a plug, connector or other type of interface that may, for example, include pin connectors or receptacles for pins) that plugs into an implantable pulse generator or some other device.

Figure 5:
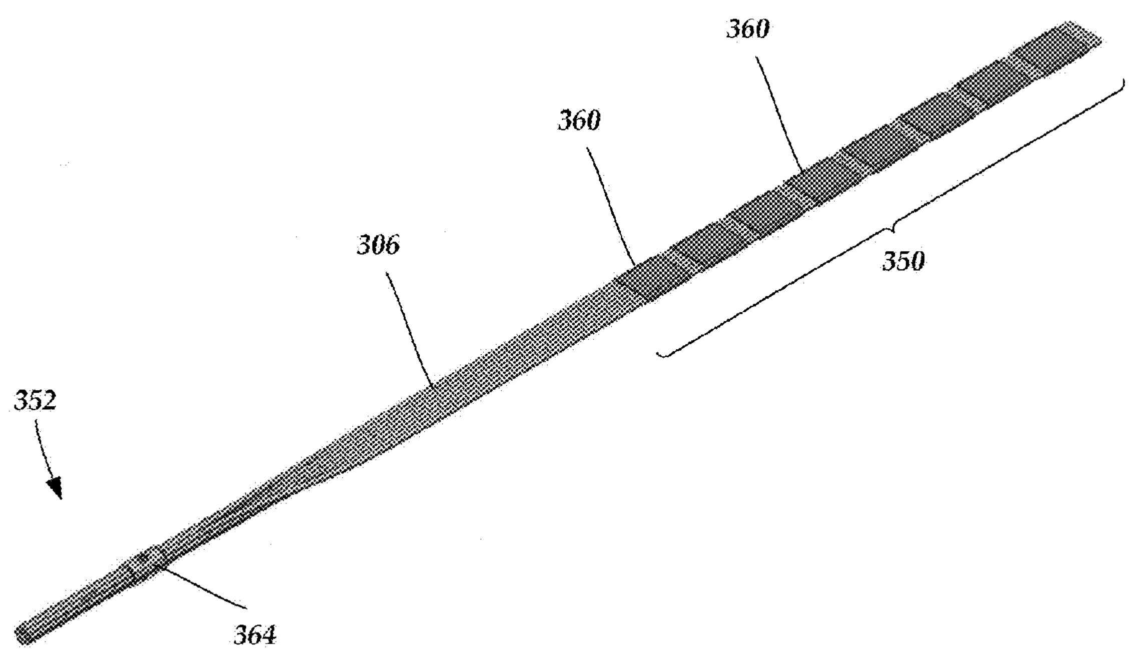
FIG. 5 is a schematic, perspective view of a lead having a ribbon cable and a plurality of conductive polymer electrodes according to an embodiment of the present invention.

FIG. 5 schematically illustrates another portion of the ribbon cable 306 that includes the distal end portion 350 and a proximal end portion 352. With regard to the distal end portion 350, a plurality of conductive electrodes 334 are placed over or applied onto the apertures 354 (FIG. 4). In at least some embodiments, the electrodes 334 take the form of conductive polymer electrodes 334 that are painted, printed, coated, attached, adhered or otherwise applied onto the apertures 354. The conductive polymer electrodes 334 may be on one side of the ribbon cable 306 or they may extend fully or partially around the ribbon cable 306 as long as such partial covering creates electrical contact between a particular electrode and an exposed conductor. For example, the conductive polymer electrodes 334 may extend at least 25, 50, 60, 75, 80, 90 or 95 percent around the ribbon cable. In at least some embodiments, the ribbon cable 306 may take the form of a flexible extrusion that may be custom shaped and varied by modifying a polymer application set-up (e.g., printing pads or painting masks).

In at least some embodiments, the conductive polymer electrodes 334 may be made from a conductive material such as, but not limited to, a silver epoxy, a carbon epoxy, a platinum epoxy, or a composite epoxy. The conductive polymer electrodes 334 may include a polymeric base mixed with conductive particulate or conductive material. The polymeric base may be made from materials such as, but not limited to, polyurethane, acrylic and silicone. In other embodiments, the polymer base is a conductive polymer that may optionally include a conductive particulate or conductive material therein. In at least some embodiments, the conductive polymer electrodes 334 are applied to the ribbon cable 306 through a timed curing process that may include, but is not limited to, a period of time, a temperature change (e.g., heat), a pressure, ultraviolet light, visible light, solvent evaporation or some combination thereof depending on the type of polymer. Optionally, other coupling techniques may be used to mechanically couple the electrodes to the ribbon cable. Additionally or alternatively, metal electrodes can be placed over the apertures 354 and mechanically coupled to the ribbon cable 306. Mechanical coupling techniques may include, but are not limited to, adhering (for example, with a conductive epoxy or other adhesive), pressing, crimping, welding, soldering, etc.

In at least some embodiments, the proximal end portion 352 includes one or more sleeves 364 placed over the ribbon cable 306 to arrange the ribbon cable into a cylindrical shape similar to current neurostimulation leads that connect to operating room cables and implanted pulse generators. Additionally or alternatively, the sleeves 364 can be conductive terminals that impart the cylindrical shape to the ribbon cable while being in electrical communication with the conductors disposed within the ribbon cable. In the aforementioned embodiments, the sleeves 364 can operate to shape the proximal end portion of the ribbon cable into a cylindrical configuration. However, the sleeves 364 may shape the proximal end portion of the ribbon cable into other cross-sectional shapes such as, but not limited to, circular, elliptical, rectangular, irregular, etc. Optionally, the proximal end portion 352 can be made in the same or a similar manner as the distal end portion 350 in which apertures are created to expose the contacts within the ribbon cable and then electrodes or terminals are place onto the apertures to be in electrical communication with the conductors of the ribbon cable. Additionally or alternatively, the proximal end portion 352 may be coupled to the ribbon cable 306 using an extension, a junction or a coupler.

Figure 6A:
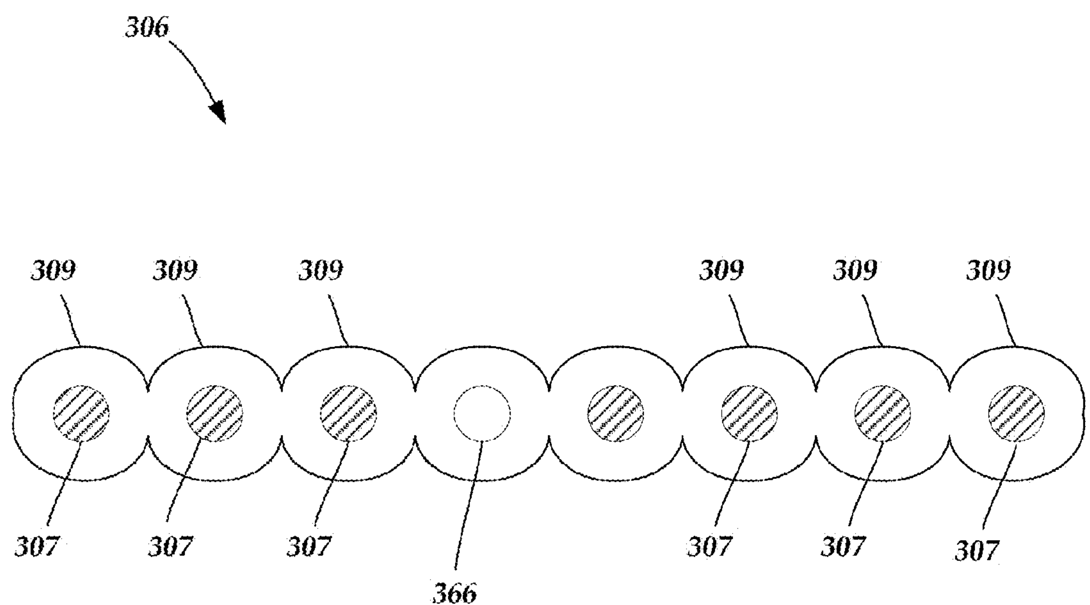
FIG. 6A is a cross-sectional view of the ribbon cable of FIG. 3B having an interior lumen according to an embodiment of the present invention.
Figure 6B:
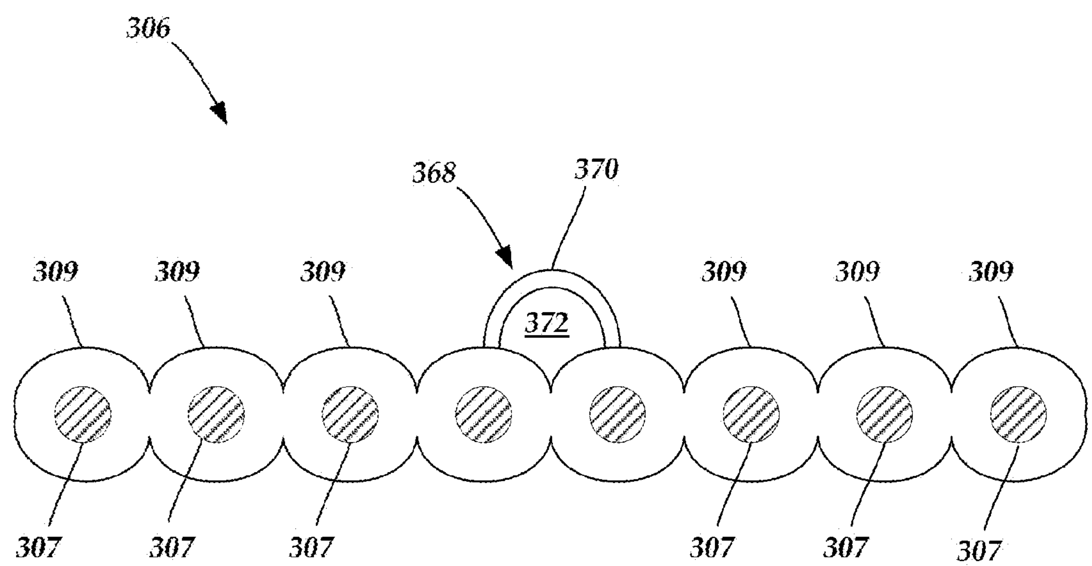
FIG. 6B is a cross-sectional view of the ribbon cable of FIG. 3B having an exterior lumen or attachment element according to an embodiment of the present invention.

In at least some embodiments, the lead 303 may be implanted using open surgical techniques or may be implanted percutaneously through a needle or plastic sheath (not shown). For either method of implant, a metal stylet wire (not shown) may be used to provide column stiffness. Referring to FIG. 6A, the stylet wire could interface with the ribbon cable 306 through an interior lumen 366 within the insulation covering of the ribbon cable. Referring to FIG. 6B, additionally or alternatively, the stylet wire could interface with the ribbon cable 306 through an exterior lumen or attachment element 368 that is attached to or formed with the insulation covering of the ribbon cable. For example, the attachment element may have a comparative length that is equal to or less than 100, 90, 80, 70, 60, 50, 40, 30, 20, 10, or 5 percent of a total length of the ribbon cable. By way of example, the exterior lumen 368 may take the form of an eyelet member 370 that defines a channel 372 to receive the stylet wire.

In at least some embodiments, the lead 303 could be used for temporarily implanted for trial therapy or may be permanently implanted. Additionally or alternatively, the lead 303 provides a low profile (e.g., thin) distal electrode form factor that may be beneficial for peripheral nerve stimulation (e.g., facial implant). Additionally or alternatively, the low profile may also permit the lead to be wrapped around physical structures such as, but not limited to, a dorsal root ganglia or vagus nerve tissues. In at least some embodiments, the lead 303 may have applications in brain neurostimulation due to its low profile, flexibility and ability to accommodate variable and complex electrode patterns or arrangements.

Figure 7:
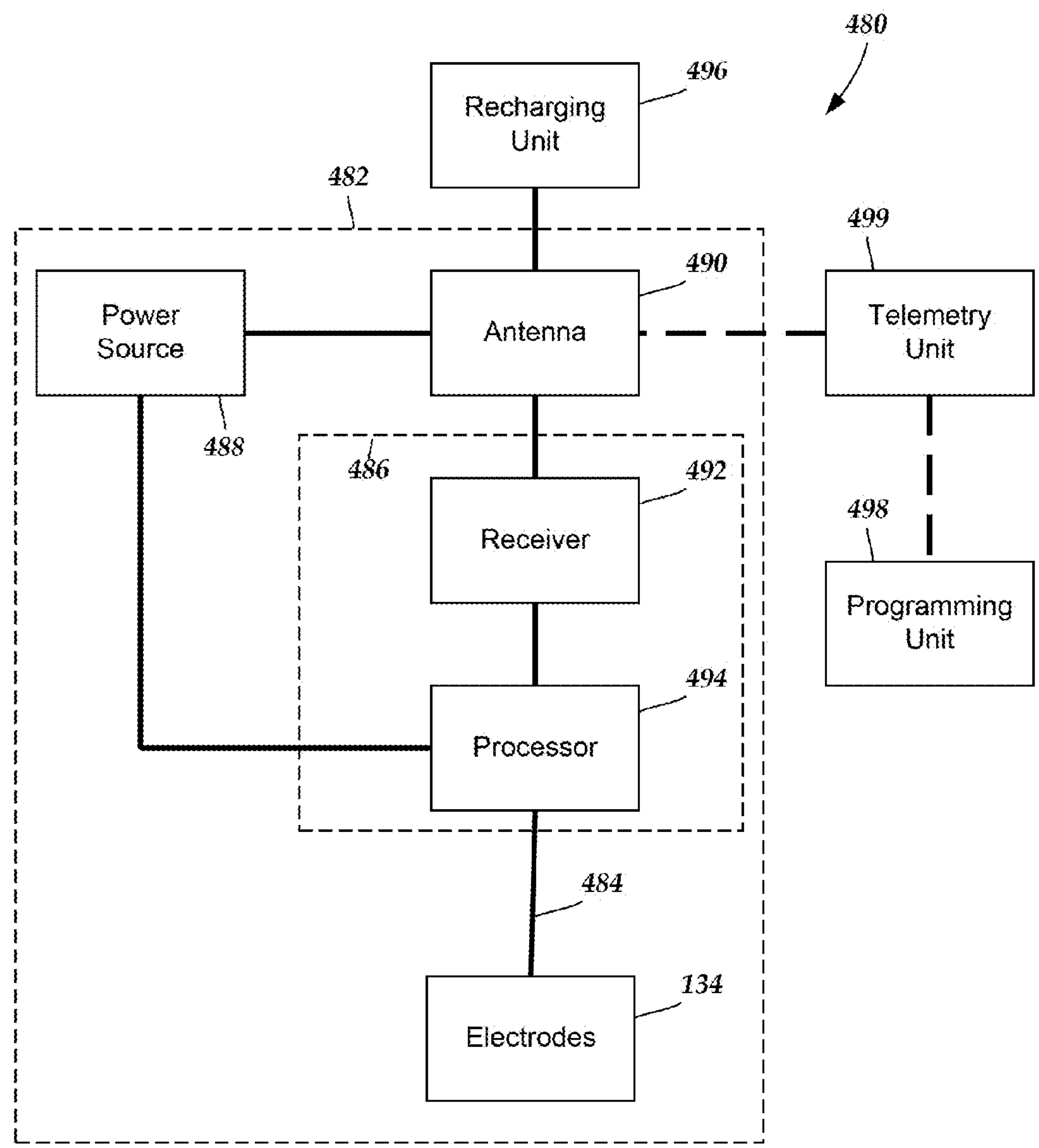
FIG. 7 is a schematic diagram of an electrical stimulation system according to an embodiment of the present invention.

FIG. 7 is a schematic overview of one embodiment of components of an electrical stimulation arrangement 480 that includes an electrical stimulation system 482 with a lead 484, stimulation circuitry 486, a power source 488, and an antenna 490. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 488 is a rechargeable battery or chargeable capacitor, the power source may be recharged/charged using the antenna 490, if desired. Power can be provided for recharging/charging by inductively coupling the power source 488 through the antenna 490 to a recharging unit 496 external to the user. Examples of such arrangements can be found in the references identified above.

In one embodiment, electrical current is emitted by the electrodes (such as electrodes 134 in FIG. 1) on the lead 484 to stimulate nerve fibers, muscle fibers, or other body tissues near the electrical stimulation system. The stimulation circuitry 486 can include, among other components, a processor 494 and a receiver 492. The processor 494 is generally included to control the timing and electrical characteristics of the electrical stimulation system. For example, the processor 494 can, if desired, control one or more of the timing, frequency, strength, duration, and waveform of the pulses. In addition, the processor 494 can select which electrodes can be used to provide stimulation, if desired. In some embodiments, the processor 494 selects which electrode(s) are cathodes and which electrode(s) are anodes. In some embodiments, the processor 494 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 498 that, for example, allows modification of pulse characteristics. In the illustrated embodiment, the processor 494 is coupled to a receiver 492 which, in turn, is coupled to the antenna 490. This allows the processor 494 to receive instructions from an external source to, for example, direct the pulse characteristics and the selection of electrodes, if desired.

In one embodiment, the antenna 490 is capable of receiving signals (e.g., RF signals) from an external telemetry unit 499 that is programmed by the programming unit 498. The programming unit 498 can be external to, or part of, the telemetry unit 499. The telemetry unit 499 can be a device that is worn on the skin of the user or can be carried by the user and can have a form similar to a pager, cellular phone, or remote control, if desired. As another alternative, the telemetry unit 499 may not be worn or carried by the user but may only be available at a home station or at a clinician's office. The programming unit 498 can be any unit that can provide information to the telemetry unit 499 for transmission to the electrical stimulation system 482. The programming unit 498 can be part of the telemetry unit 499 or can provide signals or information to the telemetry unit 499 via a wireless or wired connection. One example of a suitable programming unit is a computer operated by the user or clinician to send signals to the telemetry unit 499.

The signals sent to the processor 494 via the antenna 490 and the receiver 492 can be used to modify or otherwise direct the operation of the electrical stimulation system 482. For example, the signals may be used to modify the pulses of the electrical stimulation system such as modifying one or more of pulse duration, pulse frequency, pulse waveform, and pulse strength. The signals may also direct the electrical stimulation system 482 to cease operation, to start operation, to start charging the battery, or to stop charging the battery.

Optionally, the electrical stimulation system 482 may include a transmitter (not shown) coupled to the processor

494 and the antenna 490 for transmitting signals back to the telemetry unit 499 or another unit capable of receiving the signals. For example, the electrical stimulation system 482 may transmit signals indicating whether the electrical stimulation system 482 is operating properly or not or indicating when the battery needs to be charged or the level of charge remaining in the battery. The processor 494 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A lead comprising:

a ribbon cable comprising a distal end portion and a proximal end portion, the ribbon cable comprising an insulating body and a plurality of conductors disposed within the insulating body and extending longitudinally from the distal end portion of the ribbon cable to the proximal end portion of the ribbon cable, the ribbon cable further comprising a plurality of electrode apertures selectively disposed along the distal end portion of the ribbon cable, wherein each of the conductors is a wire or multi-filar cable; and a plurality of conductive electrodes, wherein each of the plurality of conductive electrodes is disposed over at least one of the plurality of electrode apertures and in electrical communication with at least one of the plurality of conductors.

2. The lead of claim 1, further comprising a plurality of conductive terminals selectively disposed along the proximal end portion of the ribbon cable, wherein each of the plurality of conductive terminals is in electrical communication with at least one of the plurality of conductors.

3. The lead of claim 1, wherein the ribbon cable further comprises a plurality of terminal apertures selectively disposed along the proximal end portion of the ribbon cable.

4. The lead of claim 3, further comprising a plurality of conductive terminals, wherein each of the plurality of conductive terminals is disposed over at least one of the plurality of terminal apertures and in electrical communication with at least one of the plurality of conductors.

5. The lead of claim 1, wherein the plurality of electrode apertures are staggered with respect to each other in a longitudinal direction along the insulating body.

6. The lead of claim 1, wherein at least one of the plurality of conductive electrodes is a conductive polymer electrode.

7. The lead of claim 6, wherein the conductive polymer electrode is made of a conductive epoxy.

8. The lead of claim 6, wherein the conductive polymer electrode is made of a polymeric material mixed with a conductive material.

9. The lead of claim 1, wherein at least one of the plurality of conductive electrodes extends at least from one edge of the ribbon cable to an opposite edge of the ribbon cable.

10. The lead of claim 1, wherein the distal end portion of the ribbon cable is shaped in a generally planar configuration.

11. The lead of claim 2, wherein the proximal end portion of the ribbon cable is shaped in a cylindrical configuration.

12. The lead of claim 1, wherein at least one of the plurality of conductive electrodes extends completely around the insulating body.

13. An electrical stimulation system comprising:

the lead of claim 1; and a control module comprising a housing and an electronic subassembly disposed in the housing.

14. The electrical stimulation system of claim 13, wherein at least one of the plurality of conductive electrodes is a conductive polymer electrode.

15. A lead comprising:

a flexible, flat lead body comprising a distal end portion and a proximal end portion, the lead body comprising a plurality of conductors disposed within an insulation covering with the conductors lying parallel to each other along the distal end portion, the lead body further comprising a plurality of electrode apertures selectively disposed along the distal end portion of the lead body; and a plurality of conductive electrodes, wherein each of the plurality of conductive electrodes is disposed over at least one of the plurality of electrode apertures and in electrical communication with at least one of the plurality of conductors.

16. The lead of claim 15, further comprising a plurality of conductive terminals selectively disposed along the proximal end portion of the lead body, wherein each of the plurality of conductive terminals is in electrical communication with at least one of the plurality of conductors.

17. The lead of claim 16, further comprising the lead body comprising a plurality of terminal apertures selectively disposed along the proximal end portion of the insulation covering.

18. The lead of claim 17, further comprising a plurality of conductive terminals, wherein each of the plurality of conductive terminals is disposed over at least one of the plurality of terminal apertures and in electrical communication with at least one of the plurality of conductors.

19. A method of making a lead, the method comprising:

obtaining a ribbon cable comprising a plurality of conductors disposed within an insulating body;

selectively removing regions of the insulating body to create a plurality of apertures that expose the plurality of conductors; and placing a plurality of conductive elements over the plurality of apertures, wherein each conductive element is in electrical communication with each conductor in the ribbon cable, respectively.

20. The method of claim 19, wherein placing the plurality of conductive elements over the plurality of apertures include applying a conductive polymeric material over the plurality of apertures.

* * * * *